United States Patent [19]
Kuntz et al.

[11] Patent Number: 4,966,596
[45] Date of Patent: Oct. 30, 1990

[54] LASER ATHERECTOMY CATHETER

[75] Inventors: Richard E. Kuntz; Donald S. Baim, both of Newton, Mass.

[73] Assignee: The Beth Israel Hospital Association, Boston, Mass.

[21] Appl. No.: 229,622

[22] Filed: Aug. 8, 1988

[51] Int. Cl.⁵ .............................................. A61B 17/36
[52] U.S. Cl. ......................................... 606/7; 606/15; 128/398
[58] Field of Search ..................................... 604/20–22, 604/96; 128/303.1, 395–398, 6; 606/7, 13–16

[56] References Cited

U.S. PATENT DOCUMENTS

| | | | |
|---|---|---|---|
| 4,040,413 | 8/1977 | Ohshiro | 604/101 |
| 4,249,533 | 2/1981 | Komiya | 128/303.1 |
| 4,266,547 | 5/1981 | Komiya | 128/395 |
| 4,694,828 | 9/1987 | Eichenbaum | 128/303.1 |
| 4,832,023 | 5/1989 | Murphy-Chutorian | 128/303.1 |

FOREIGN PATENT DOCUMENTS

| | | |
|---|---|---|
| 3209444 | 10/1982 | Fed. Rep. of Germany ... 128/303.1 |
| 8804157 | 6/1988 | PCT Int'l Appl. .................. 128/398 |

*Primary Examiner*—Stephen C. Pellegrino
*Assistant Examiner*—Ralph Lewis
*Attorney, Agent, or Firm*—Lorusso & Loud

[57] ABSTRACT

Method to remove an eccentric vascular obstruction by excision with laser energy, preferably excimer laser energy, delivered through a mobile fiber optic shelf, and collecting the excised section within a housing.

Apparatus to perform a surgically smooth excision of an eccentric vascular obstruction whereby a mobile fiber optic shelf delivers excimer laser energy to the obstruction to sever the obstruction from the vessel wall, a housing collects the excised section through a radially located cut-out window, the mobile fiber optic shelf traps the excised section within the housing, and a laser light collector prevents the escape of laser energy after application to the obstruction wherein the excised obstruction is physically removed from a patient's body.

12 Claims, 8 Drawing Sheets

LASER ATHERECTOMY CATHETER

BACKGROUND OF THE INVENTION

This invention relates to a method and apparatus for removing vascular obstructions, such as atheromatous plaque and thrombi. More particularly, the invention relates to the use of a laser, preferably an excimer laser, for performing surgically smooth excisions of eccentric obstructions and containing the excised section.

Several techniques exist for enlarging an obstructed arterial lumen. The most common procedure is known as balloon angioplasty. Using this technique, the artery is dilated by inflating a balloon catheter within the lumen of the artery. The angioplasty balloon reduces arterial obstruction by eccentrically displacing atheromatous lesions through vessel wall dissection. The inadequacies of balloon dilation relate to the fact that the technique fractures, but does not physically remove, atheromatous plaque. The resulting roughened arterial surface causes the formation of blood clots (thrombi). In addition, the continued presence of the atheromatous material in the artery acts as a nucleus for the redeposition of additional atheromatous material (restenosis). Approximately 20–30% of arteries treated with balloon dilation experience restenosis within 6 months.

Another device for displacing vascular obstructions, called a "cut-and-retrieve" system, is described in U.S. Pat. No. 4,669,469, issued June 2, 1987, for a "Single Lumen Atherectomy Catheter Device". The balloon inflatable device uses a fixed guidewire attached at its tip for positioning within the blood vessel. Properly positioned, the device causes prolapse of an eccentric vascular obstruction into the cavity of a metal housing attached to a vascular catheter. The metal housing is essentially an enlarged cylindrical cavity having a cut-out window and a cup-shaped blade positioned just below this window. A balloon is located opposite from the window such that inflating the balloon pushes the window against the arterial wall causing prolapse of the eccentric obstruction into the cavity of the metal housing. A section of the obstruction is then excised by the rotating blade as it is advanced along the length of the window. The excised section is contained within the housing and is physically removed from the patient's body. By physically removing the atheromatous material and leaving a surgically smooth arterial wall surface, the incidence of restenosis is reduced. Unfortunately, the mechanical requirements of a housing able to contain a high speed (about 2,000 r.p.m.) rotating blade have largely left this catheter to be efficacious in only large peripheral arteries. Although a coronary version has been recently designed, it is cumbersome and cannot reach secondary coronary branches.

The smallest mechanical atherectomy catheter available has an outside diameter of 5 French. A catheter of this size requires an 11 French guiding catheter for insertion into an artery. The practical limitations on such a mechanical device are due to the difficulty in miniaturizing the mechanical parts and the inherent rigidity of a metal housing. The metal housing is necessitated by the presence of a rotating blade. Thus, the large metal housing associated with the catheter excludes the use of this device in small, tortuous vessels.

Laser atherectomy devices, on the other hand, can be as small as the laser optic component delivering the laser energy. In general, laser atherectomy involves directing a catheter, adapted to transmit laser energy, into a blood vessel and advancing the free end of the catheter within the blood vessel to the location of an occlusion or arteriosclerotic plaque. The catheter delivers laser energy to the location to vaporize the occlusion, thereby opening obstructed blood vessels.

The use of the intense and concentrated energy of a laser within a portion of the body, such as a blood vessel, presents the danger of damage to the surrounding tissue. In the case of a blood vessel, possible perforation of the blood vessel is a primary concern.

Atherectomy methods which utilize laser energy for treating vascular obstructions can be categorized as direct or indirect techniques. Direct ablation of atheromatous material usually produces prothrombotic thermal charring and surrounding acoustic or "blast" injury to the adjacent vessel wall The relatively long wavelengths associated with $CO_2$, Nd:YAG, and argon lasers (10.6 u, 1.06 u, and 0.5 u respectively) contain minimal energy with which to cut through plaque material. Thus, such lasers must "hack away" at the obstruction leaving behind a ragged surface and producing a significant amount of thermal energy that can damage the surrounding vessel.

In comparison, the excimer laser has a shorter wavelength and a higher energy which enables it to vaporize tissue instantly without burning or causing acoustic injury. Excimer lasers utilize an inert gas and halogen gas medium and emit at a wavelength in the ultraviolet range. The power associated with the excimer laser (and rapidly pulsed, high energy lasers of longer wavelengths) is much more focused than the above lasers and permits ablation of the plaque before any heat is transmitted to the surroundings.

The direct use of lasers within arteries, however, is further hampered by the fact that lasers cannot distinguish plaque from the normal wall of the artery and, ultimately, perforate the arterial wall. Efforts to reduce the incidence of arterial perforation due to direct laser techniques are aimed at improving the sensitivity of plaque over normal wall (including spectral analysis, and tetracycline or hematoporhyrin staining), and at improving the delivery of laser energy along the vessel lumen (using guidewires, centralizing balloons, or angioscopic visualization of the laser fiber). None of these techniques provides a practical solution to safe ablation of plaque, sparing normal vessel wall, to date.

U.S. Pat. No. 4,207,874, issued June 17, 1980, for a "Laser Tunneling Device" is an example of a catheter having a bundle of optical fibers. The catheter is adapted to be advanced within a blood vessel to a point which is adjacent to an occlusion or calcified plaque for the application of the laser energy. Suction is applied to the laser to remove the debris resulting from the vaporization of the occlusion.

U.S. Pat. No. 4,240,431, issued Dec. 23, 1980, for "Laser Knife" discloses a device using laser energy for the incision or excision of an affected part of the body. In order to prevent the laser energy from causing undesirable cautery or piercing of normal tissue adjacent that which is to be treated, the laser energy is intercepted by a receiving surface, once the cutting procedure is completed.

U.S. Pat. No. 4,685,458, issued Aug. 11, 1987, for "Angioplasty Catheter and Method for Use Thereof" discloses a device having a pair of abutments disposed on the outer surface of the distal portion of a catheter. A fiber optic, either a bundle of glass fibers or a single fiber, has a distal end portion disposed within one abutment. The fiber optic is adapted to transmit laser energy from a source which is intercepted by the second abutment. A suction port disposed between the pair of abutments removes the debris from the site of the plaque at the inner surface of the blood vessel. The device has an inflatable bladder which causes the pair of abutments to contact the inner surface of the blood vessel. The device may be rotated about the central axis of the blood vessel. Removal of the plaque or occlusion is observed by fluoroscopy or taking a pressure gradient observation across the lesion.

The configurations of the direct laser atherectomy catheters described above do not provide for the positive containment of the resulting excised obstruction. Positive containment is a more reliable method of trapping all liberated obstructions and, thus, minimizes the potential for distal coronary embolization or loss of material into the systemic arterial circulation. It also avoids the possibility of suction-induced injury to the vessel wall.

Another drawback to the above laser atherectomy techniques is that the optical fibers are immobilized at one end of the obstruction. Thus, the delivered laser energy, which decreases in intensity over distance, merely chips away or disintegrates the obstruction, generating small particles. The small particles which easily elude capture may subsequently cause blockages in small blood vessels. The small particles which are captured are useless for diagnostic analysis. Retrieval of excised sections is an important diagnostic tool for determining the proximity of the excised section to the vessel wall and for distinguishing specimens of atheromatous plaque from thrombi specimens. The former function is useful to determine the extent of excision; the latter function is useful for prescribing post catheterization treatment.

Indirect laser techniques involve the controlled delivery of thermal energy to the diseased vessel. Examples of indirect thermal treatment include a catheter with a laser-heated metallic tip to "melt" plaque and a specially designed balloon catheter with light-diffusing fiber. The disadvantage of these treatment methods is that they merely reshape, rather than remove, plaque. Thus, these devices resemble balloon angioplasty more so than atherectomy, although the use of heat may leave behind a smoother surface than conventional angioplasty. See Sanborn, T.A., 55 *J. Am. Coll. Cardiol.* 934-38 (1985).

It is clear that a method is needed to enlarge arterial lumens that is more effective than angioplasty, more widely applicable than mechanical "cut-and-retrieve" systems, and safer than current direct and indirect laser techniques. A preferred treatment for vascular obstructions must minimize or correct local injury responsible for abrupt vessel reclosure and physically remove and/or leave behind a smooth luminal surface in an effort to reduce the incidence of thrombosis or restenosis. It is also clear, however, that while direct application of high energy lasers has the capacity to make surgically smooth excisions through atheromatous plaque, the risk of arterial perforation is great. Thus, an apparatus and method which prevent arterial perforation without detracting from the effectiveness of the direct application of laser energy is desired. Finally, a laser technique that collects excised obstructions suitable for diagnostic analysis and that controls the occurrence of debris entering the blood stream is needed.

SUMMARY OF THE INVENTION

In accordance with the present invention, it has been discovered that vascular stenosis and thrombosis are more effectively treated by removing obstructions with laser energy, specifically, excimer laser energy, compared to balloon dilation, mechanical "cut-and-retrieve" systems, and other laser atherectomy techniques. The present invention utilizes a mobile means for delivering laser energy through an obstruction, a means for collecting the excess laser energy, and a means for retrieving the excised section for diagnostic purposes. Because the apparatus may be constructed from a flexible material and because the size of the apparatus is limited only by the means for delivering the laser energy, the present invention may be applied to intrinsically tortuous arteries as well as to large peripheral arteries.

Accordingly, the present invention is a percutaneous technique to remove vascular obstructions from vessel walls. A catheter is inserted into a patient's artery over a guidewire. A housing is located at a distal end of the catheter having an enlarged diameter, a cut-out window which exposes a housing cavity to an adjacent wall, and an inflatable balloon attached to an exterior surface opposite from the window. A mobile fiber optic shelf is positioned within the housing just proximal to the window. The mobile fiber optic shelf may be formed from a fiber optic bundle flattened at one end. A second end of the fiber optic bundle is connected to a laser energy source. Fluoroscopy is used to position the window over an eccentric obstruction. When inflated, the balloon causes prolapse of the eccentric vascular obstruction through the window and into the housing cavity. The mobile fiber optic shelf cuts through the obstruction as it is advanced across the window and traps the severed section within the housing. When the mobile fiber optic shelf reaches a laser light collector device at a point distal to the window, the obstruction is excised by laser energy, trapped within the housing cavity, and retrievable.

It is therefore an object of the present invention to provide a method to excise and retrieve vascular obstructions from both large peripheral arteries and intrinsically tortuous arteries.

It is another object of the present invention to provide a method to reduce arterial obstructions which minimizes or corrects local injury responsible for vessel reclosure.

It is a further object of the present invention to provide a method to excise vascular obstructions which leaves a surgically smooth lumenal surface.

It is another object of the present invention to provide a method to excise vascular obstructions using laser energy without causing perforation of the arterial wall.

It is yet another object of the present invention to provide a method to excise and remove vascular obstructions suitable for diagnostic analysis which prevents debris from entering the blood stream and clotting smaller vessels by retaining the excised portion of an obstruction immediately after excision and removing it from a patient's body.

DESCRIPTION OF THE PREFERRED EMBODIMENTS

At the outset, the present invention is described in its broadest overall aspects with a more detailed description following. The broadest aspects of the invention involve positioning a modified catheter under a vascular obstruction, covering the obstruction with a housing, delivering laser energy, preferably excimer laser energy, through a mobile fiber optic shelf, trapping the excised section within the housing with the mobile fiber optic shelf, and retrieving the excised section contained in the housing.

The present invention builds on the discovery that laser energy can be delivered through small fiber optic bundles. Incorporating laser technology within an atherectomy catheter minimizes the catheter's outer diameter and, thus, expands the range of applications to include small, tortuous arteries. The excimer laser is preferred because of the efficient manner in which it can bore through atheromatous material such that a surgically smooth inner arterial wall surface results. A smooth inner surface prevents the formation of blood clots and the redeposition of atheromatous material on the vessel wall. In addition, an excimer laser can ablate atheromatous plaque with less surrounding thermal and acoustic injury than lasers at longer wavelengths.

The present invention also builds upon a mechanical "cut-and-retrieve" system which collects the excised section of a vascular obstruction in a housing cavity for retrieval from a patient's body. The mechanical system, however, utilizes a rotating blade to excise lesions and is difficult to miniaturize. The rotating blade necessitates a metal housing in order to avoid damaging a blood vessel. This limitation excludes application of such a system to small, tortuous arteries.

Figure 1:
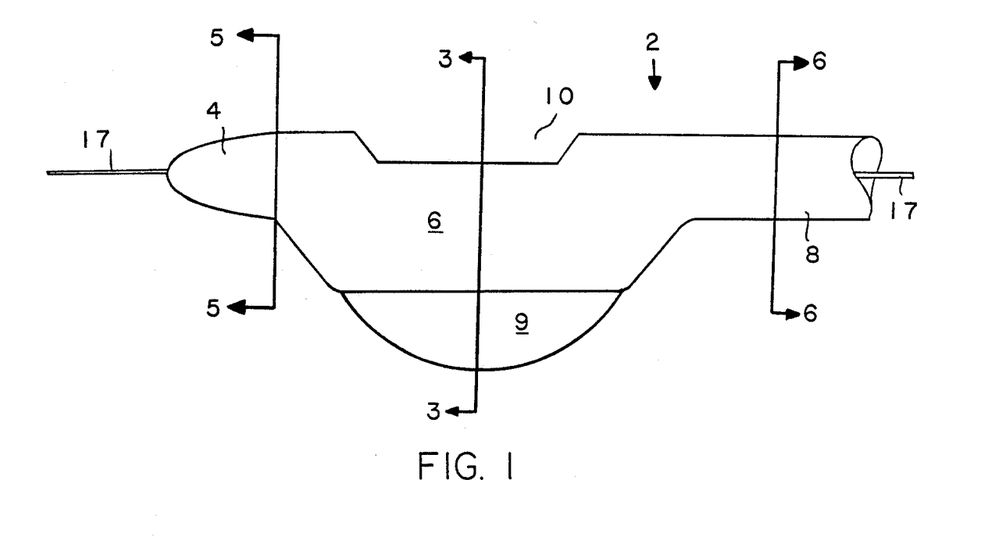
FIG. 1 is a side plan view of the catheter of the present invention.

The laser atherectomy catheter of the present invention is shown in FIG. 1. The catheter 2 can be manufactured as one unit having three regions a tip 4, a housing 6, and a tail 8. The catheter 2 is formed in th conventional manner and of a conventional flexible material. The tip 4 is the most distal portion of the catheter when inserted in a patient's body. The housing 6 has an outer diameter that is larger than the diameter of either the tip 4 or the tail 8. A balloon 9 is attached to the housing 6 and surrounds a portion of the housing 6 which is opposite from a cut-out window 10. The balloon 9 is a conventional balloon as employed in balloon angioplasty. It is secured to the exterior of the housing 6 by a suitable means such as an adhesive.

Figure 2:
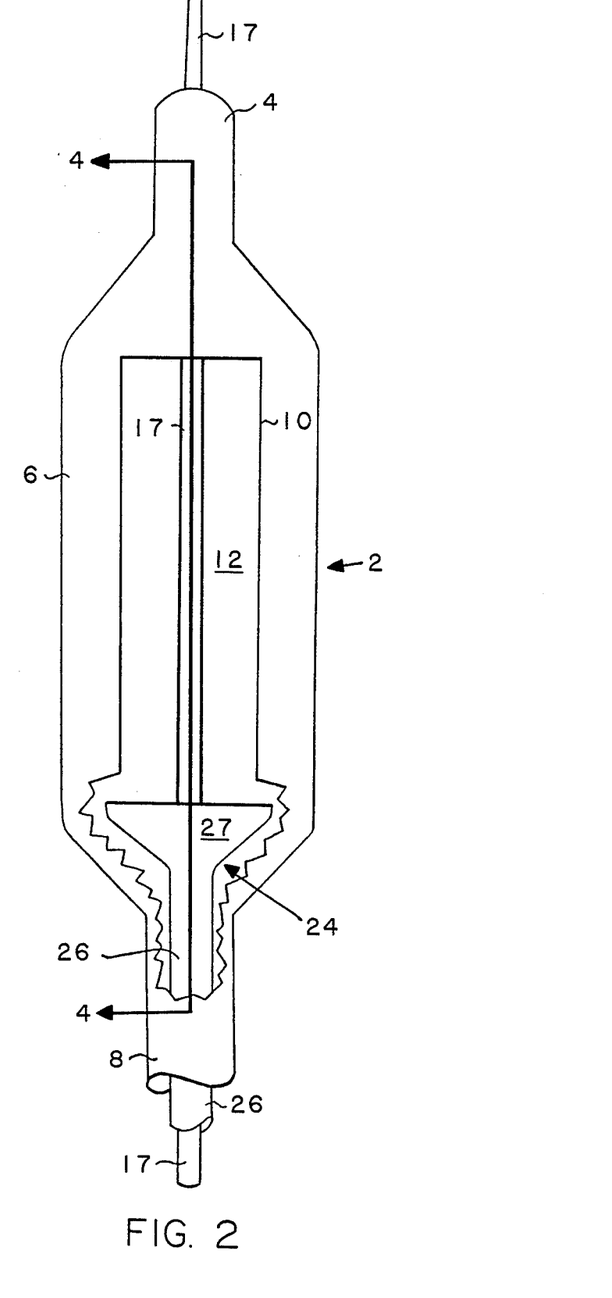
FIG. 2 is a top plan view of the catheter of the present invention showing the cut-out window of the housing with a cutaway view showing a preferred embodiment of the mobile fiber optic shelf wherein the flattened portion of the mobile fiber optic shelf has a minimum length needed to splay a fiber optic bundle to a desired width.
Figure 3:
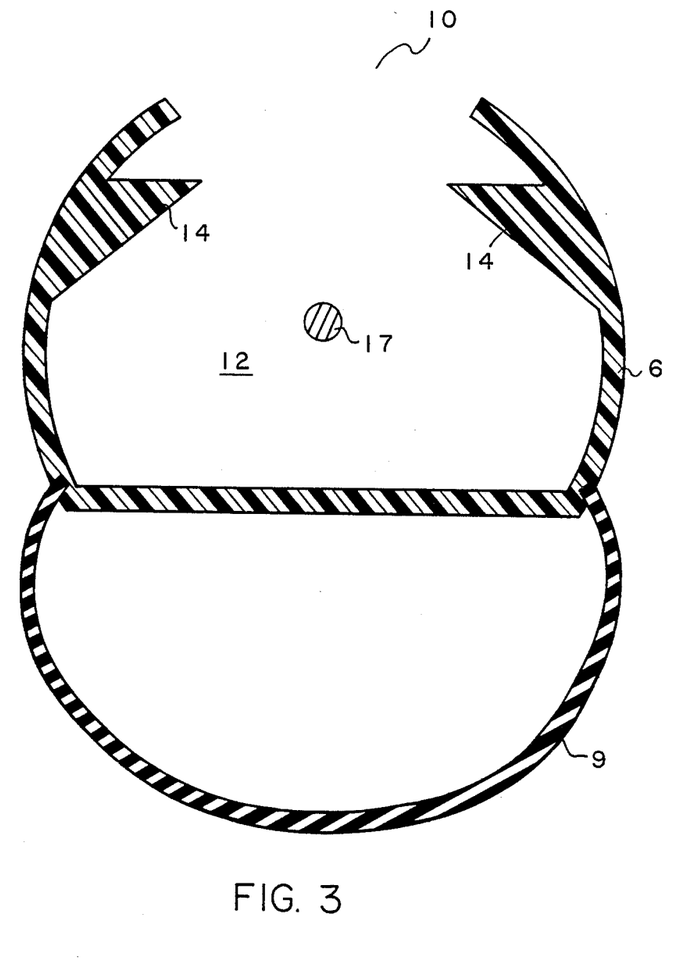
FIG. 3 is an enlarged cross-sectional view of the catheter of the present invention taken along the line 3—3 of FIG. 1.
Figure 4:
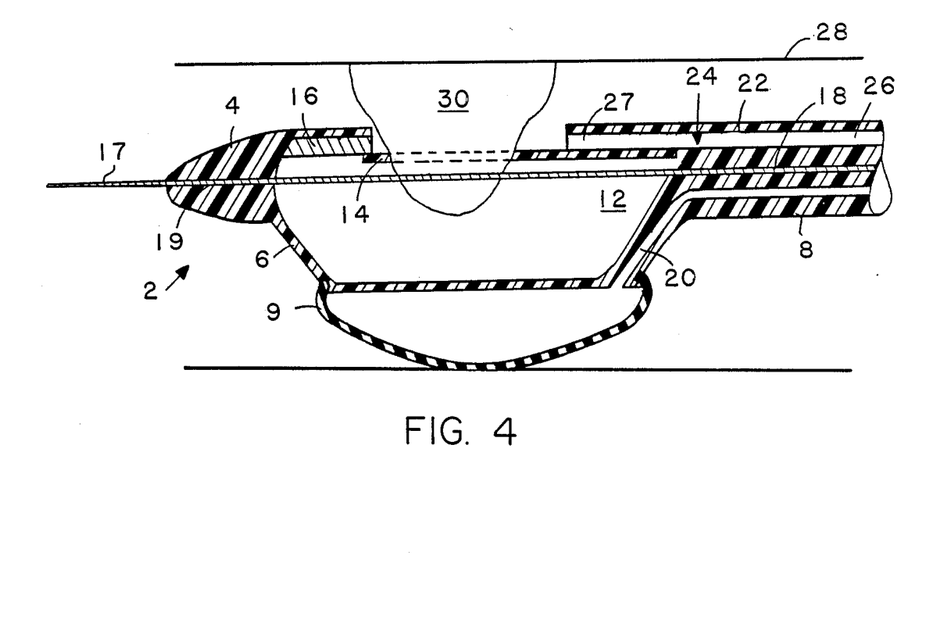
FIG. 4 is cross-sectional view of the catheter of the present invention prior to the excision of an obstruction taken along the line 4—4 of FIG. 2.

As shown in FIG. 2, a radially located cut-out window 10 exposes a housing cavity 12. Below the window 10, two guiding ledges 14, 14' (best shown in FIG. 3) are formed within the housing cavity 12. Referring to FIG. 4, a laser light collector 16 is connected to the underside of the housing 6 at the distal end of the window 10 and the guiding ledges 14, 14'. The laser light collector 16 is constructed from an unablatable material which is capable of absorbing or reflecting excimer laser energy at close range without causing damage to the vessel wall or to the device. By way of example, the laser light collector 16 may be constructed from a polished steel ring.

Figure 5:
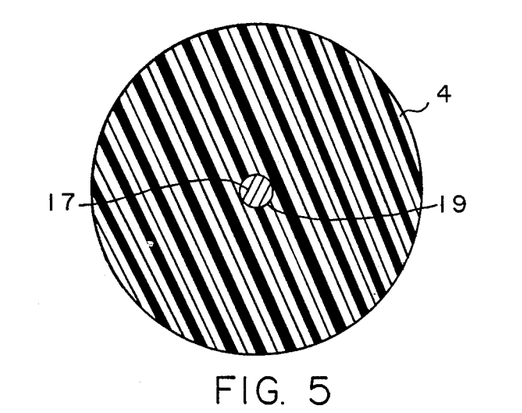
FIG. 5 is an enlarged cross-sectional view of the catheter of the present invention taken along the line 5—5 of FIG. 1.
Figure 6:
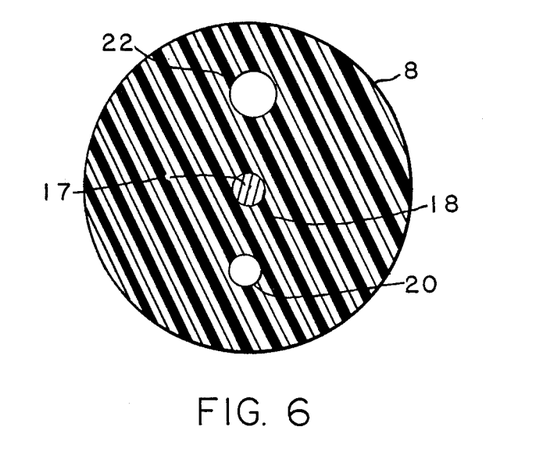
FIG. 6 is an enlarged cross-sectional view of the catheter of the present invention taken along the line 6—6 of FIG. 1.
Figure 7:
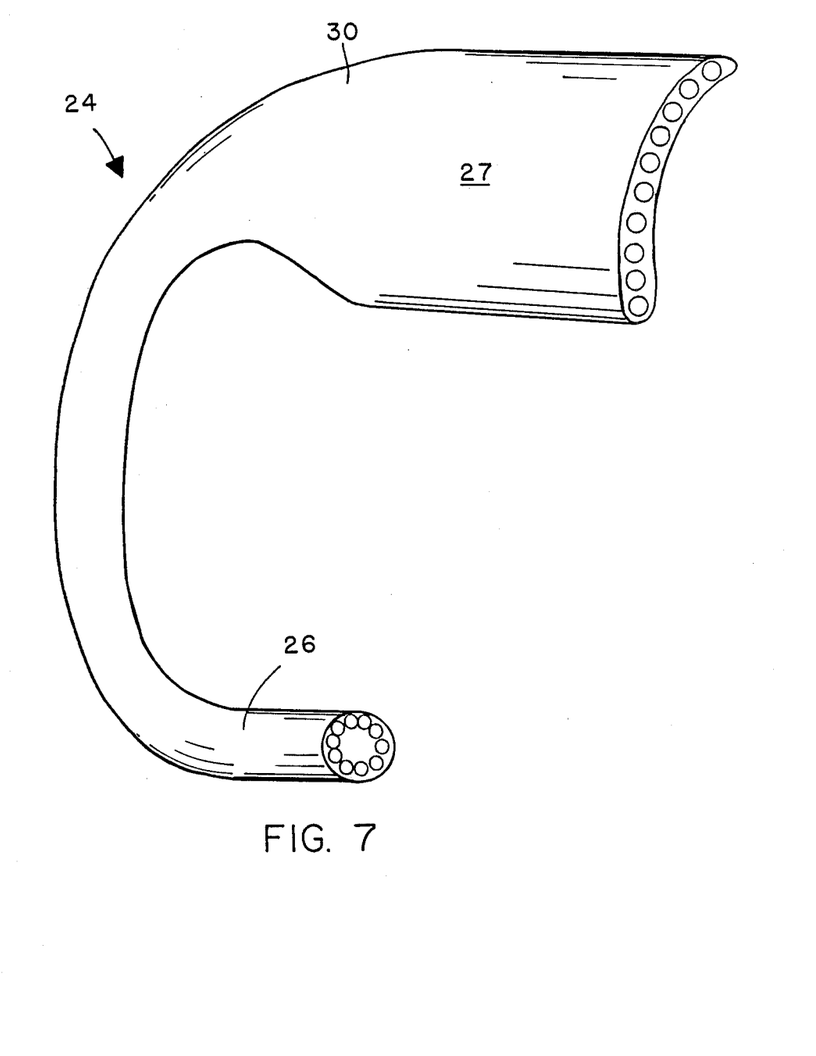
FIG. 7 is a view of the mobile fiber optic shelf formed from a mobile fiber optic bundle flattened at one end; and, FIG. 8 is a top plan view of the catheter of the present invention showing the cut-out window of the housing with a cutaway view showing an embodiment of the mobile fiber optic shelf wherein the flattened portion of the mobile fiber optic shelf has a width that can be accommodated within a fiber optic port.

A conventional flexible elongated guidewire 17 is removably mounted in the atherectomy device. The guidewire 17 extends through a guidewire port 18, through the housing cavity 12 and through a lumen 19 defined by the tip 4 (see FIG. 5). As shown in FIGS. 4 and 6, a balloon port 20 and a fiber optic port 22 largely parallel the guidewire port 18 in the tail 8. The balloon port 20 exits the housing 6 at a point opposite the window 10 such that the balloon 9 may be inflated with a fluid, such as radiographic contrast solution, through the balloon port 20. The fiber optic port 22 houses a mobile fiber optic shelf 24 and directs the mobile fiber optic shelf 24 onto the guiding ledges 14, 14'. The mobile fiber optic shelf 24 may be embodied by a fiber optic bundle 26 having a flattened portion 27 at one end (see FIG. 7). A second end of the mobile fiber optic shelf 24 is connected to a laser energy source (not shown). An excimer laser is the preferred laser energy source.

The flattened portion 27 of the mobile fiber optic shelf 24 has a slightly larger width than the cut-out window 10 so that the flattened portion 27 is movably braced between the guiding ledges 14, 14' and the housing 6. The flattened end 27 can have a width that is either smaller or larger than the width of the fiber optic port 22, but in all cases, the width of the flattened portion 27 is larger than that of the window 10.

Figure 8:
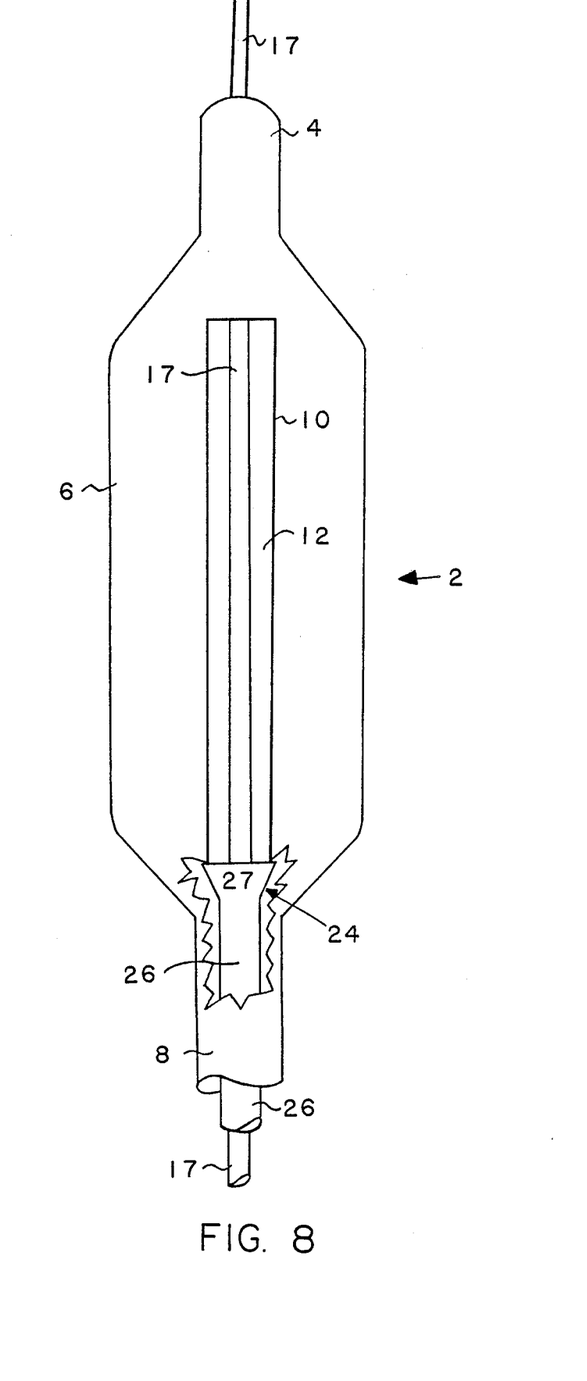

In one embodiment, shown in FIG. 8, the flattened portion 27 of the mobile fiber optic shelf 24 has a width that can be accommodated within the fiber optic port 22

(not shown). At the same time, the width of the flattened portion 27 remains larger than the width of the cut-out window 10. This design permits the insertion of the fiber optic shelf 24 through the fiber optic port 22, either before or during use of the catheter 2. The flattened portion 27 shown in FIG. 8 also has a minimum length needed to splay a fiber optic bundle to a desired width.

Figure 9:
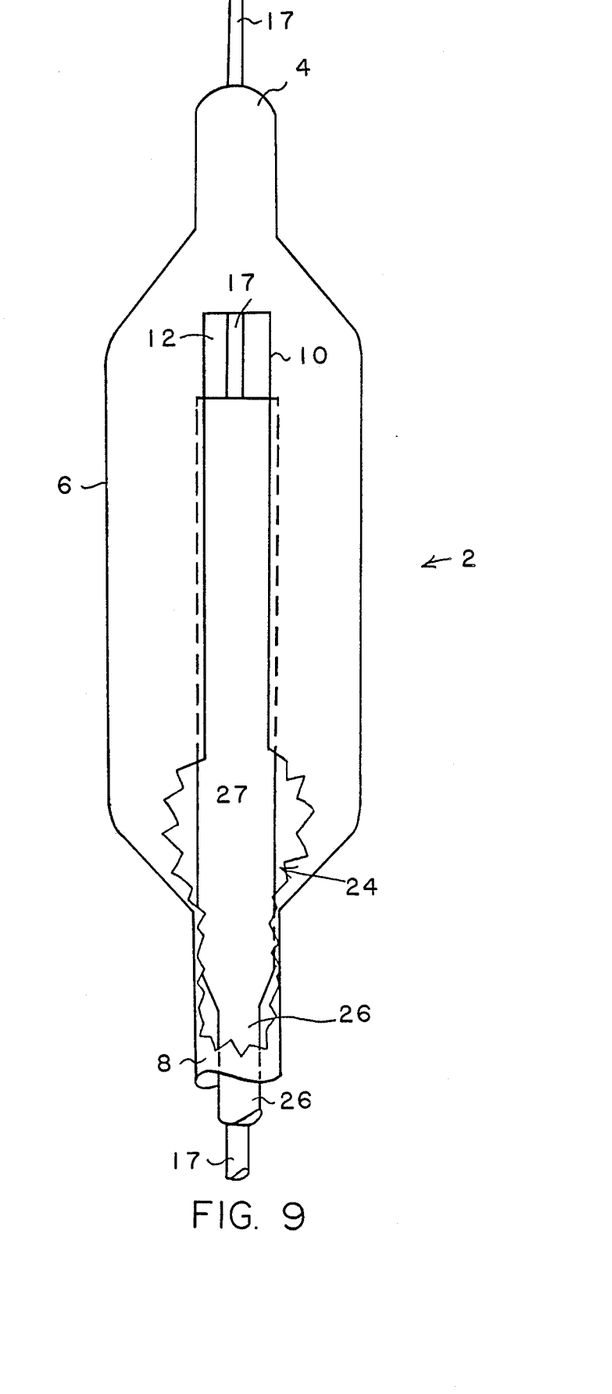
FIG. 9 is a top plan view of the catheter of the present invention showing the cut-out window of the housing with a cutaway view showing an embodiment of the mobile fiber optic shelf wherein the flattened portion of the mobile fiber optic shelf has a length that is greater than a minimum length needed to splay a fiber optic bundle to a desired length.

In another embodiment, shown in FIG. 9, the flattened portion 27 has a width as shown in FIG. 8 and a length that is greater than a minimum length needed to splay a fiber optic bundle to a desired width This embodiment permits more complete enclosure of the housing cavity 12 by the flattened portion 27 of the mobile fiber optic shelf 24 for the retention of excised atheroma. However, complete enclosure of the housing cavity 12 by the flattened portion 27 is not required for adequate retention of the excised atheroma within the housing cavity 12.

In a preferred embodiment, shown in FIG. 2, the flattened portion 27 of the mobile fiber optic shelf 24 has a minimum length needed to splay a fiber optic bundle to a desired width and a width that is greater than the width of the fiber optic port 22 (not shown). A mobile fiber optic shelf 24 having this configuration can be inserted into the fiber optic port 22 through the cut-out window 10 in preparation of treatment. In this manner, the flattened portion 27 does not travel through the fiber optic port 22, but, rather, remains within the housing 6 and is initially positioned at a proximal end of the cut-out window 10. Thus, although the flattened portion 22 may not be accommodated within a fiber optic port 22, it occupies a very small space within the housing 6 at a proximal end of the cut-out window 10 prior to treatment. Consequently, the cut-out window 10 can have a width that is greater than that of the embodiment shown in either FIG. 8 or FIG. 9.

The advantage associated with this embodiment relates to the fact that the flexibility of the housing 6 is increased as the size of the cut-out window 10 is increased. In addition, larger slices of atheroma may be removed from a vascular lumen. While this embodiment does not allow for the complete enclosure of the housing cavity 12 by the flattened portion 27, it does provide sufficient retention of excised atheroma slices within the housing cavity 12 by the mobile fiber optic shelf 24. Therefore, an optimal configuration of the catheter 2 maximizes both the length and the width of the window 10.

Prior to the use of the catheter device of the present invention, the location of an undesired material, such as an occlusion or an accumulation of plaque or other lesions within a blood vessel of the patient, is first determined by conventional techniques such as angioscan, X-ray, and/or tomography. Thereafter, a puncture can be made in the femoral artery, by way of example, and a guidewire is then advanced through a guiding catheter positioned in the coronary ostium, and advanced down the vessel to the vicinity of the occlusion or accumulation of plaque. The catheter device of the present invention can be advanced to the desired location over the guidewire and through the guiding catheter to the location of the plaque. In the alternative, access to the region of a blockage can be attained during an operation, for example, during open-heart surgery. Once the incision is made in the blood vessel in question, known techniques, such as those involving fluoroscopy or angioscopy, can be used to observe the condition within the blood vessel which is to be treated by use of the catheter device of the present invention.

Figure 10:
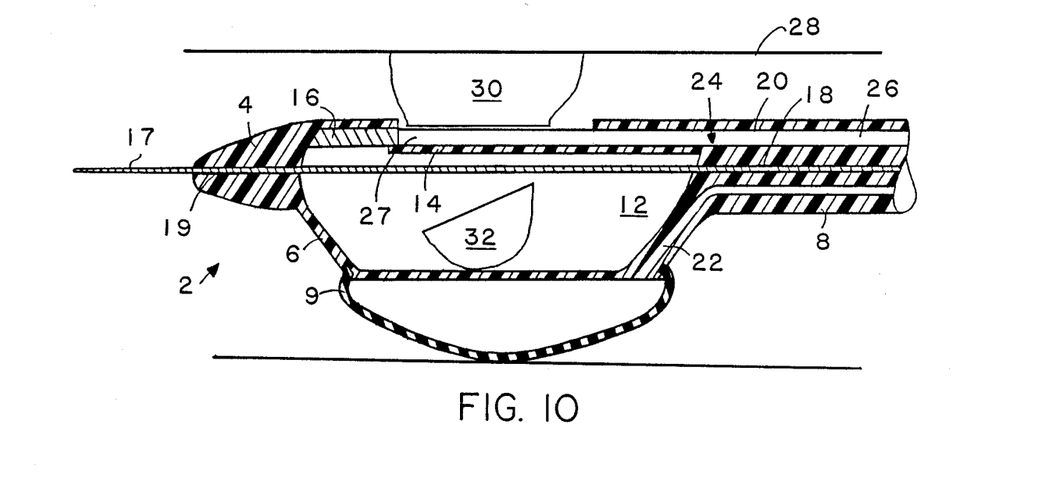
FIG. 10 is a cross-sectional view of the catheter of the present invention within an artery after excision of an obstruction.

The method of the present invention is shown in FIGS. 4 and 10. In practice, a guidewire 17 is inserted into a patient's artery 28 beyond an obstructed region within the artery. The atherectomy catheter 2 is advanced over the guidewire 17 and is positioned under an eccentric obstruction 30 using fluoroscopy. Fluid pressure is then applied to the balloon 9 causing the prolapse of the obstruction 30 into the housing cavity 12.

The fluid used to inflate the balloon 9 may be a dilute radiographic contrast solution. This is the standard fluid used in present angioplasty methods. The use of radiographic contrast solution in the balloon 9 helps to identify the position of the balloon 9 and the cut-out window 10 for the precise placement over an atherosclerotic lesion designated for removal.

Excimer laser pulses emanating from the laser energy source are delivered through the mobile fiber optic shelf 24 and are directed towards the obstruction 30. The mobile fiber optic shelf 24 is then advanced down the guiding ledges 14, 14' as it cuts through the obstruction 30 until it reaches the laser light collector 16. In this manner, the intensity of the laser energy available to cut through the obstruction 30 is maximized. The mobile fiber optic shelf 24 stays in contact with the guiding ledges 14, 14' because of the close fit between the guiding ledges 14, 14' and the housing 6 and because the flattened portion 27 of the mobile fiber optic shelf 24 has a greater width than the window 10. Thus, the catheter of the present invention prevents the misdirection of laser light which might cause arterial perforation. The catheter of the present invention also provides consistently high intensity laser energy to the obstruction at all points along the path of excision, thus the length of the excision path is not restricted to the distance that the laser energy can travel.

When the mobile fiber optic shelf 24 reaches the laser light collector 16, as shown in FIG. 10, the excised section 32 falls into the housing cavity 12. The mobile fiber optic shelf 24 covers the window 10 such that the housing cavity 12 is no longer completely exposed to the arterial lumen 42. In this manner, the excised section 32 is retained within the housing cavity 12. The catheter 2 is then removed from the patient's body along with the retained, excised section 32. This procedure may be repeated several times until the obstruction is essentially removed.

Figure 11:
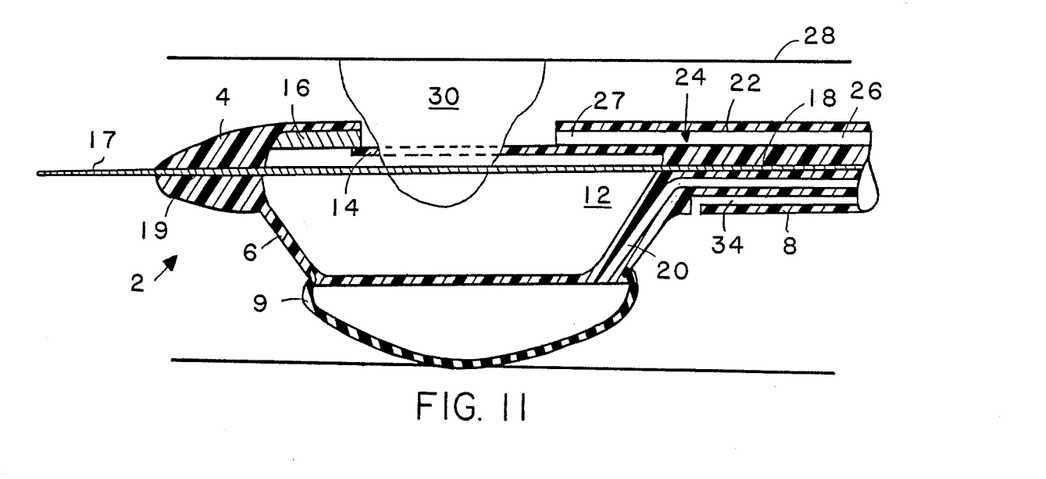
FIG. 11 is a cross-sectional view of the catheter of the present invention within an artery prior to excision of an obstruction showing the dye port for visualizing the interior of the artery.

An alternative practice entails injecting radiographic dye through a dye port 34 (see FIG. 11) in the catheter 2 in order to visualize the residual obstruction using radiographic techniques. This procedure obviates the need to remove the catheter from the patient's body after each pass to determine completion of the operation. An empirical decision might also be made after studying preliminary angiogram results to determine the number of passes that can be made before the cavity is filled and the excision is completed.

Composite analysis of the excised portion 32 can be performed between passes to discern its distance from the arterial wall. In this manner, the treating physician is able to determine the requisite number of passes to complete the operation. The excised section 32 can also be analyzed so as to distinguish atheromatous plaque from blood clots. Once the excised section is identified as such, post operative treatment can be designed in accordance with this diagnosis.

This procedure is most efficient when the focused power of the excimer laser is utilized. The ability of the excimer laser energy to make surgically smooth excisions through atheromatous material with haste prevent potentially injurious heat loss to the surroundings. Furthermore, the risk of arterial wall perforation in using the direct treatment of the present invention is eliminated by the incorporation of a laser light collector 16 and guiding ledges 14, 14' which prevent the misdirection of laser energy.

The laser atherectomy catheter of the present invention does not include any mechanical elements, thus the housing 6 may be manufactured from a flexible, nonmetallic material. In comparison, the atherectomy catheter according to U.S. Pat. No. 4,669,469 contains a rotating blade which necessitates a metal housing and, thus, limits its applications to large arteries. The elimination of a rotating drum permits the construction of a flexible, smaller-sized atherectomy catheter (less than 5 French). The smaller, more flexible catheter of the present invention has a wide range of uses from small, tortuous arteries to larger, peripheral arteries.

A second advantage of the present invention over U.S. Pat. No. 4,669,469 is that the free space within the housing cavity 12 is not reduced by an advancing, rotating drum. The catheter of the present invention therefore allows for a larger collection of excised obstructions per retrieval.

A third advantage of the present invention is that the portion of the plaque which remains on the arterial wall after excision is cauterized by the laser activity. Cauterization denatures possible thrombogenic proteins and is the speculated method of non-thrombogenesis.

Another advantage is that positive containment of the excised section is a more reliable method of trapping all removed plaque than suctioning procedures described in U.S. Pat. Nos. 4,207,874 and 4,685,458. In addition to minimizing the potential for distal coronary embolization, positive containment avoids the potential for suction-induced injury to the vessel wall Finally, excising and retrieving portions of the obstruction of a size suitable for pathologic analysis provides a diagnostic tool for the post operative treatment of the patient. This advantage is not realized with other laser atherectomy devices that disintegrate the obstruction and suction out the debris.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and there is no intention to exclude any equivalents thereof. Hence, it is recognized that various modifications are possible when within the scope of the present invention as claimed.

What is claimed is:

1. A method to remove an eccentric vascular obstruction from a patient comprising the steps of:
    inserting a guidewire into an artery to a point beyond an eccentric vascular obstruction;
    inserting a catheter over said guidewire into the artery, said catheter having a housing including a radially located cut-out window on one surface, said cut-out window exposing a housing cavity, and a balloon attached to an opposite exterior surface, said housing containing a mobile bundle of fiber optic cables, said bundle being flattened at an end of the bundle proximal to the cut-out window and said bundle connected to a laser energy source at an opposite end;
    positioning said cut-out window over said eccentric vascular obstruction;
    inflating the balloon such that the eccentric vascular obstruction extends through said cut-out window into said housing; and
    delivery laser energy across said cut-off window while advancing said flattened end of the mobile bundle of fiber optic cables across said cut-off window to excise and to retain the eccentric vascular obstruction within said housing.

2. The method of claim 1 wherein excimer laser energy is delivered across the cut-out window while advancing said mobile bundle of fiber optic cables across said cut-out window.

3. A method to remove an eccentric vascular obstruction from a patient comprising the steps of:
    inserting a guidewire into an artery to a point beyond an eccentric vascular obstruction;
    inserting a catheter having a dye port over said guidewire into said artery, said catheter having a housing including a radially located cut-out window on one surface, said cut-out window exposing a housing cavity, and a balloon attached to an opposite exterior surface, said housing containing a mobile bundle of fiber optic cables, said bundle being flattened at an end of the bundle proximal to the cut-out window and said bundle connected to a laser energy source at an opposite end;
    injecting a radiographic dye through said dye port for visualizing the eccentric vascular obstruction;
    positioning said cut-out window over said eccentric vascular obstruction;
    inflating the balloon such that the eccentric vascular obstruction extends through said cut-out window into said housing; and
    delivering laser energy across said cut-out window while advancing the flattened end of said mobile bundle of fiber optic cables across said cut-out window to excise and to retain the eccentric vascular obstruction within said housing.

4. The method of claim 3 wherein excimer laser energy is delivered across the cut-out window while advancing the flattened end of said mobile bundle of optic fiber cables across said cut-out window.

5. An apparatus to excise and remove an eccentric vascular obstruction from an artery in a patient comprising:
    a catheter defining a housing having a radially located cut-out window on one surface, said cut-out window exposing a housing cavity, and a balloon attached to an opposite exterior surface;
    a means for inflating said balloon in fluid communication with said balloon;
    a means for delivering laser energy across said radially located cut-out window, said means for delivering laser energy disposed at one end of said radially located cut-out window and being mobile across the window and comprising a bundle of fiber optic cables that is inserted through a fiber optic port located in the housing, connected to a laser energy source at one end, and flattened at a second end proximal to the cut-out window; and
    a means for collecting said laser energy positioned at a second end of said radially located cut-out window;

wherein when the catheter is positioned in an artery, the balloon is inflated such that the cut-out window encompasses the eccentric vascular obstruction, the mobile means for delivering laser energy delivers such energy along a path of excision to excise a portion of the eccentric vascular obstruction, the portion them being retained within said housing, for removal from the patient.

6. The apparatus of claim 5 wherein said means for inflating the balloon comprises a balloon port through which balloon port a fluid can be delivered to the balloon.

7. The apparatus of claim 5 wherein said flattened end of the mobile bundle of fiber optic cable has a width that is greater than the width of the cut-out window.

8. The apparatus of claim 7 wherein said flattened end of the mobile bundle of fiber optic cables has a length that is at least as long as the length of the cut-out window.

9. The apparatus of claim 7 wherein said flattened end of the mobile bundle of fiber optic cable has a width that is greater than the width of the fiber optic port and has a minimum length.

10. The apparatus of claim 5 wherein said flattened end of the mobile bundle of fiber optic shelf has a width that is greater than the width of the cut-out window and that can be accommodated within the fiber optic port.

11. The apparatus of claim 10 wherein said flattened end of the mobile bundle of fiber optic cables has a length that is at least as long as the length of the cut-out window.

12. The apparatus of claim 10 wherein said flattened end of the mobile bundle of fiber optic cables has a minimum length.

* * * * *